United States Patent [19]

Viehmann et al.

[11] Patent Number: 5,537,875
[45] Date of Patent: Jul. 23, 1996

[54] ULTRASONIC METHOD FOR THE INSPECTION OF SPAT WELDS BETWEEN METAL PLATES

[76] Inventors: Hans Viehmann, Kolner Ring 130, D-5042, Erfstadt; Klaus Volkmann, Feldstrasse 121 a, D-5060, Bergisch Gladbach 2, both of Germany

[21] Appl. No.: 325,316
[22] PCT Filed: Apr. 20, 1993
[86] PCT No.: PCT/DE93/00343
  § 371 Date: Dec. 22, 1994
  § 102(e) Date: Dec. 22, 1994
[87] PCT Pub. No.: WO93/21524
  PCT Pub. Date: Oct. 28, 1993

[30] Foreign Application Priority Data

Apr. 22, 1992 [DE] Germany .................. 42 13 212.6

[51] Int. Cl.⁶ ............................................. G01N 29/10
[52] U.S. Cl. ............................................. 73/588
[58] Field of Search ................................. 73/588, 602, 629

[56] References Cited

U.S. PATENT DOCUMENTS

| | | | |
|---|---|---|---|
| 4,208,917 | 6/1980 | Aoyama et al. | 73/588 |
| 4,265,119 | 5/1981 | Dubetz et al. | 73/588 |
| 4,428,235 | 1/1984 | Sugiyama | 73/602 |

*Primary Examiner*—John E. Chapman
*Attorney, Agent, or Firm*—Quarles & Brady

[57] ABSTRACT

In the ultrasonic-inspection method proposed, a high-frequency test probe with a transducer diameter equal to the nominal diameter of the spot weld to be inspected is coupled, through an input path, with the plates in the vicinity of the spot weld and, using the pulse/echo method, the plates are irradiated with ultrasonic waves and the echo pulse trains received are evaluated. In each case, the spectral line corresponding to the overall-thickness propagation time is examined for sufficient minimum amplitude (energy density) and for sufficient minimum width (damping).

13 Claims, 1 Drawing Sheet

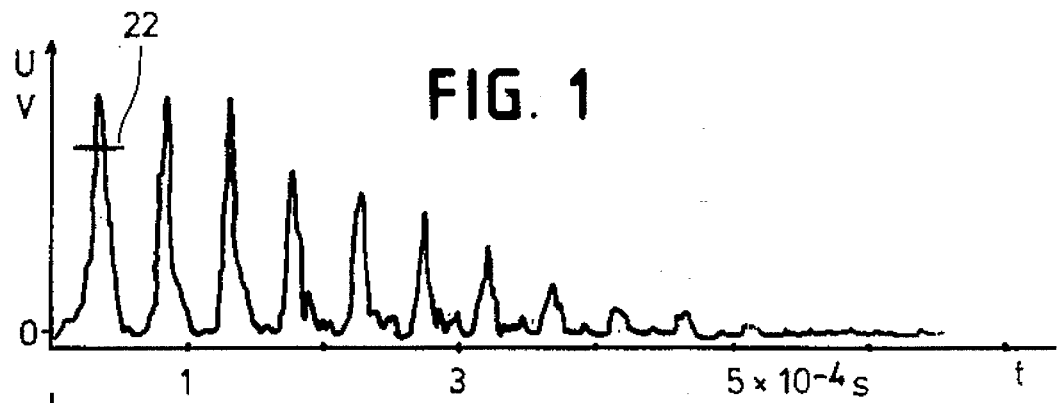
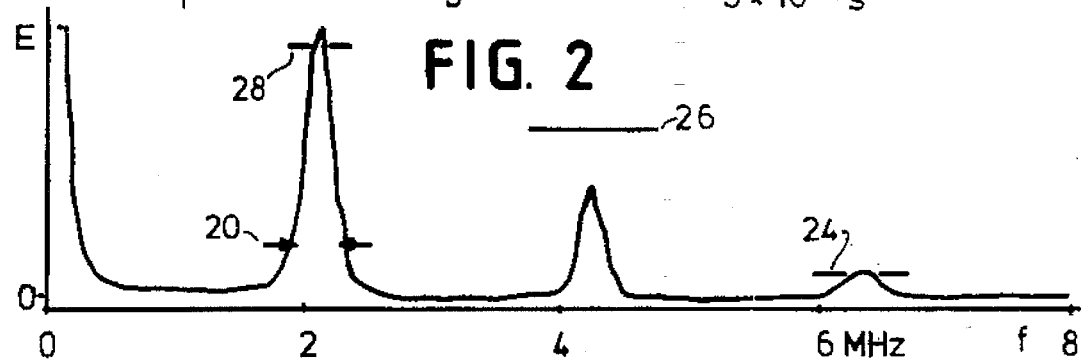
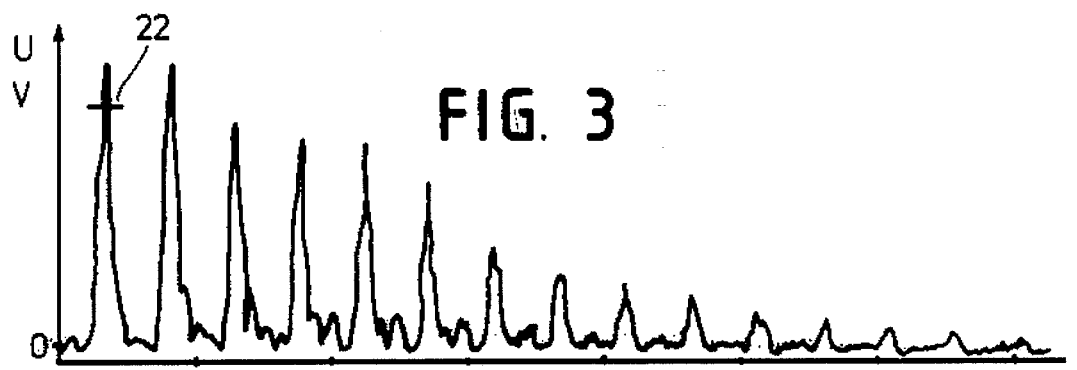
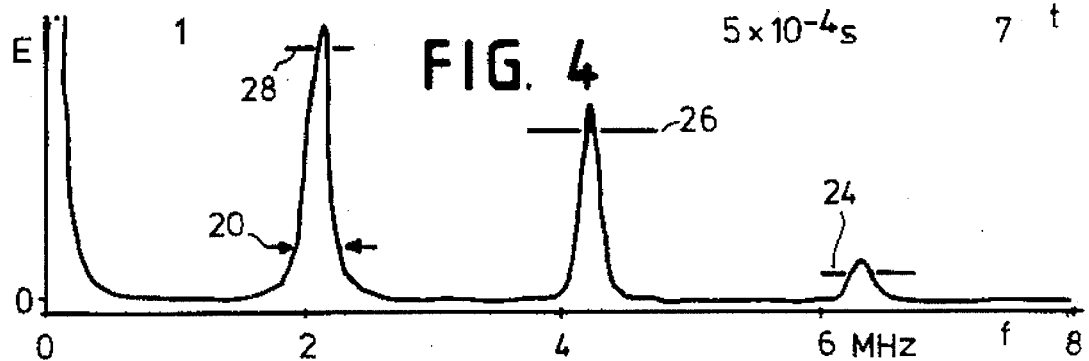

5,537,875

ULTRASONIC METHOD FOR THE INSPECTION OF SPAT WELDS BETWEEN METAL PLATES

The invention relates to a method for the ultrasonic inspection of point welds of metal sheets or plates, in which a high-frequency test probe with a transducer diameter equal to the nominal diameter of the point weld to be inspected is coupled, with a lead section, to the sheets in the vicinity of the point weld and, using the pulse/echo method, the sheets are irradiated with ultrasonic signals and the echo pulse train corresponding to overall-thickness is evaluated.

The inspection of point welds is described in the book J. Krautkrämer and H. Krautkrämer "Werkstoffprüfung mit Ultraschall" (Ultrasonic testing of materials) 4th ed., pp. 505 and 506. According to this book the inspection of point welds between two sheets involves vertical testing and acquisition of the multiple echoes of the overall thickness. If the lenticular weld joint (welding spot) is well developed, a relatively short echo pulse train results from the overall thickness of the weld jointed sheets, because of the high attenuation (damping) of sound at the coarse grain of the welding spot solidified from the melt. A cold weld on the other hand entails a longer echo pulse train from the overall thickness due to the fine grain of the sheet with significantly lower attenuation of sound; the interface between the two surfaces does not reflect in a typical cold weld. In general a very long multiple echo train results from an ideal cold weld. Too small a volume of the welding spot causes the multiple echo train to lengthen as well, as the path traveled by the sound pulse within the fine-grain sheet becomes longer and the path through the more strongly attenuating grain of the welding spot becomes shorter. At the same time a shift of the ultrasonic frequency occurs. If there is no joint whatsoever between the sheets, no echo pulse train results from overall thickness. In that case there is only the echo pulse train for the single sheet thickness of the coupled single sheet.

In passenger car manufacturing, standard spot diameters of welding spots are between 3.6 and 5.5 mm. The transducer diameters of the test probes are dimensioned accordingly. The test probe frequency is in the MHz region, for example at 15 MHz. Coupling is effected with a lead section of synthetic material or water.

Proper operation of the test probes is of special importance. Proper irradiating conditions are only obtained with a precise vertical coupling of the test probe and transmission of sound through the center of the welding spot. During practical testing this is achieved by slightly shifting the test probe laterally into the center of the welding spot and lining it up vertically, to be identified by the intermediate echo train from the single sheet thickness(es) reaching a minimum. The shortest possible echo pulse train from the overall thickness and the smallest possible echo pulse train from the single sheet thicknesses indicate that the optimal positioning and thus the optimal irradiation conditions for the test probe have been obtained. Non-optimal irradiation conditions may entail a measuring result indicating an inadequate weld joint for a possibly good weld point; or, when the test probe is improperly lined up, the absence of defect echoes resulting from strong attenuation may create the incorrect impression of a good weld point.

The evaluation of echo pulse trains on the screen of an ultrasonic device is difficult and demands great experience on the part of the examiner. This in turn means that objective results cannot always be achieved.

This is where the invention comes in. Its object is to further develop the ultrasonic inspection method of the type mentioned initially in such a way, that it becomes suitable for automatically monitoring the quality of point welds between metal sheets.

Taking as a basis the method of the type mentioned initially, the invention suggests the following solution: the frequency spectra of the echo pulse trains are calculated and for each measurement the spectral line corresponding to the overall-thickness travel time is examined for a sufficient minimum amplitude on the one hand and a sufficient minimum width on the other hand.

In the frequency spectrum the spectral line with the lowest frequency is the spectral line corresponding to the overall-thickness travel time. In the case of equally thick weld jointed sheets its first harmonic coincides with the zero-th order spectral line from the single sheet thicknesses. The narrower is the spectral line from the overall thickness, the smaller is the attenuation of the echo pulse train from the overall thickness and thus the longer is this echo pulse train in the time-domain representation. If a certain minimum width is attained, then this will indicate an echo pulse train, which does not surpass a certain length (decay time).

The existence of the spectral line for the overall-thickness travel time proves that there is some joint between the two sheets. If this spectral line additionally surpasses the minimum amplitude, then this will indicate that the joint between the two single sheets is of a sufficiently large area.

Thus the minimum amplitude and the minimum width of the spectral line from the echo pulse train of the overall-thickness travel time enable the quality of a point weld to be reliably judged. Automatic monitoring of the quality of a point weld is possible by setting two threshold values for the said spectral line, this will yield a basically correct judgment which can be improved by additional but not required measures.

In summary the invention has realized, that the analysis of one spectral line from the frequency spectrum of the complete echo pulse train enables the quality of a point weld joint to be judged. This one spectral line from the overall-thickness travel time (resp. its harmonics) contains the information on the decay of the echo pulse train from the overall thickness in the time-domain representation (A-image) and on the relative size of these echo pulses in relation to other echoes, for example a back-wall echo. The advantage of the representation in the frequency spectrum lies in the clear separation of this information from the information on the single-thickness travel times. This enables an evaluation without recourse to a human observer.

In point welds three main classes of defects occur, which are reliably detected by the method according to the invention: if the two sheets are not weld-jointed to each other the spectral line of the overall-thickness travel time will be absent, and thus the required minimum amplitude will not be reached. If the two sheets are merely adhesively jointed the spectral line from the overall-thickness travel time will occur, but its width will be too small (corresponding to the low attenuation of the echo pulse train in the time-domain representation). Finally, if the welding spot is too small, or an otherwise sufficiently large welding spot has an internal defect, then too the width of the spectral line will be too small; moreover a shift of carrier frequency occurs in these cases.

In the practical execution of the method according to the invention as a first step the threshold value for the amplitude of the spectral line from the overall-thickness travel time and the threshold value for its width as well as the reference frequency for hf-evaluation are determined by comparison with sample point welds, the quality of which is exactly known. In this way an exact identification with actual geometrical properties in the welding spot is possible. Afterwards the inspection device calibrated in this way is used in the actual inspection of unknown weld joints. The amplitude is evaluated with respect to the first back-wall echo.

In a further embodiment including an additional step, the amplitude ratio between the spectral line from the overall-thickness travel time and at least one equivalent spectral line from a single-sheet-thickness travel time is measured. This ratio yields a measure of the total area of the welding spot. The greater the ratio, the larger is the area of the welding spot.

It is further suggested to assign a threshold value not only to a minimum width but also a threshold value to the maximum width of the spectral line from the overall-thickness travel time. If the spectral line from the overall-thickness travel time surpasses a certain width, there will be no proper echo pulse train for the echoes from the overall thickness and/or irradiation conditions are not optimal. Shifting the test probe will tell which is the cause.

The width of the spectral line is measured in a well known way in a certain relative height, such as for example 50%, 63% or the like of the maximum amplitude.

Moreover it has proven advantageous to represent the complete echo pulse train in the time-domain (A-image) before the calculation of the frequency spectrum. This has the advantage that the computational operation of a Fourier transform, which is still costly with present means, is only started, when the A-image has already shown that an echo pulse train from the overall-thickness travel time is present.

It is further suggested for optimal frequency resolution that the evaluation of the Fourier transform be limited to a frequency range, which contains at least the second harmonic of the spectral line from the overall-thickness travel time.

Further advantages and characteristics of the invention arise from the further claims and the description below of embodiments, not to be regarded as restrictive, of the method according to the invention. In the following this will be explained in greater detail with reference to the drawing. The drawing shows in:

FIG. 1 a diagram of the time history of the complete echo pulse train (A-image); voltage U (in volts) is plotted over time t, FIG. 2 the corresponding Fourier transform, i.e. the representation in the frequency spectrum, both for a good weld point; energy density E is plotted over frequency f, FIG. 3 a diagram corresponding to FIG. 1 for too small a weld point, and FIG. 4 a diagram corresponding to FIG. 2 for this weld point.

The figures show frequency representations or spectra of the rectified ultrasonic signal. In practice the use of the high frequency spectrum, that is the spectrum of the non-rectified signal and thus of the hf-signal, has established itself as advantageous. Explanations accompanying FIGS. 1 through 4 can also be applied to the case of a hf-signal, as the spectral lines occur axially symmetric about the carrier frequency. For rectified ultrasonic signals the value zero is to be used as carrier frequency.

The vicinity of a point weld joint between two equally thick sheets of the same material is irradiated with an ultrasonic pulse from a 15 MHz test probe with fixed input path and a transducer diameter of approx. 3 mm. The echo pulses obtained are picked up by the same test probe, amplified in an ultrasonic device, rectified and digitized, and then evaluated in a computer. By means of a computer program spectra and/or A-images are selectively displayed. The evaluation program contains evaluation criteria which will be explained below. If all of these criteria are met, a signal, for example a buzzing sound, will classify the inspected weld joint as good.

By means of the evaluation program as a first step the A-image (FIG. 1 or 3) is examined to determine if the first echo after the front-surface echo is a back-wall echo, i.e. if its travel time corresponds to the combined thickness of the two sheets to be joined by welding. If such a back-wall echo does not occur, the two sheets are not jointed or the test probe is completely outside of the weld point to be inspected. Then the first three to four echo pulses from the overall thickness are analyzed for monotonous decay. If there is no monotonous decay this will indicate an improper positioning of the test probe. In both cases (no back-wall echo or no monotonous decay of the first three or four echoes from the overall thickness) the evaluation program will output a signal requesting a better positioning of the test probe. A Fourier transform for the calculation of the spectra according to FIGS. 2 and 4 will only be performed, when, firstly, back-wall echoes from the overall thickness are observed and, secondly, when the first three to four echoes from the overall thickness show a monotonous decay.

Before computing the Fourier transform the digitally stored time-domain data (corresponding to the A-image) are reduced to reduce calculation time. Additionally tapering is performed at the beginning and at the end of the time interval used for evaluation. In the embodiment discussed a cosinus-roll-off taper is applied. In this way, step functions at the beginning and at the end of the time interval can be avoided which would create artifacts in the frequency domain. In the case of the rectified time-domain signals displayed in FIG. 1 or 3 the frequency band is limited from 0 MHz to 8 MHz.

In the time-domain representations (FIGS. 1 and 3) the front-surface echo has been muted. Therefore it does not enter into the computation of the Fourier transform.

The spectral representations according to FIGS. 2 and 4 show the energy densities E as a function of frequency f. In the course of the evaluation by the computer both the widths and the relative maxima of the respective spectral lines are used to infer judgments.

In order to obtain as high a resolution as possible in the frequency domain with a predetermined quantity of data to be processed, a reduction in the quantity of acquired data is desirable. Data are averaged in the time-domain in order to avoid aliasing of the spectral distribution by high frequency signal components in the course of data decimation and in order to suppress noise components. Spectral data are interpolated to render the calculation of amplitude ratios and line widths more exact.

For example, the first spectral line characterizing the back-wall echoes from the overall sheet thickness in the case of jointed sheets is observed at approximately 2 MHz, when the overall sheet thickness is 1.4 mm. In the case of two sheets which are not jointed this spectral line does not occur, rather the spectral line from the coupled single sheet occurs, which is observed at approximately 4 MHz. In addition to these spectral lines their harmonics are observed as well.

The width of a spectral line from the total travel time, that is e.g. approx. 2 MHz, characterizes the attenuation and allows to discriminate between a proper welding spot with sufficient attenuation and too small a welding spot or an adhesive joint of the two sheets. In the example presented in FIGS. 1 and 2 a good weld joint is shown. The width of the spectral line is determined by means of a threshold symbolized by arrows 20. The height of the spectral line is evaluated by means of a threshold 28. It can be seen in FIG. 2 that the spectral line in the selected height is wider than the threshold marked by arrows 20. This is not the case in FIG. 4, where the spectral line is narrower than the established threshold. The example presented in FIGS. 3 and 4 represents the case of an adhesive joint. Too small a welding spot will result in a similar picture as FIGS. 3 and 4; further, too small welding spots often give rise to an increase of the intermediate echoes with increasing time.

The parameters of threshold 20 are determined in preliminary experiments. To this end a number of point welds are examined both by means of ultrasonic inspection and by means of another measuring method, for example by chiselling or cutting open, or the like. The same sheets and other welding parameters are used as in the point welds to be inspected later. A minimum width of threshold 20 and its height on the energy density scale can be determined from these preliminary experiments.

The optimal position of the test probe with respect to a weld joint, i.e. the optimal irradiation conditions, can be checked in the time and/or the spectral representation: in the time-domain the best possible monotonous decay of the back-wall echoes is sought in order to be sure that the largest possible region of the welding spot is penetrated. If in addition the first back-wall echo pulse surpasses a minimum (threshold 22) with a predetermined total amplification of the ultrasonic device, then the irradiation conditions are at least fair (but leave room for improvement.) Poor irradiation conditions result in a steeply descending echo pulse train and, in the frequency domain, to a broadening of the spectra line. In the frequency domain the irradiation conditions can be determined by monitoring the widths of the first and the second spectral lines (FIGS. 2 and 4) and by setting a threshold for the energy density of the first harmonic of overall thickness (third spectral line somewhat above 6 MHz). This threshold is designated by reference symbol 24 in FIGS. 2 and 4. If the third spectral line surpasses threshold 24, the irradiation conditions will be adequate.

The following method has also established itself as specially suitable for the determination of optimal irradiation conditions, i.e. the optimal positioning, in the frequency representation: two spectral lines are considered, on the one hand the first spectral line from the overall sheet thickness (total sheet thickness travel time) and on the other hand a higher order spectral line which is not perturbed by the single sheet thickness, i.e. an odd number spectral line, for example the third spectral line. The ratio of this higher order spectral line to the first spectral line is to be as high as possible. Optimal irradiation conditions and hence an optimal positioning have been achieved, when the optimum of this ratio has been found. This method can also be applied to the ratio between higher order spectral lines, for example the fifth to the third spectral line.

Another threshold 26 is shown in FIGS. 2 and 4, it is associated with the second spectral line. If the second spectral line remains below this threshold 26, as is the case for FIG. 2 but not for FIG. 4, this means that the signal from the single-sheet travel times is sufficiently small, i.e. that on the one hand the irradiation conditions are in order and on the other hand the weld point is probably in order as well. Lateral shifting of the test probe will tell, if the resulting change in irradiation conditions will cause the energy density of the second spectral line to increase. Optimal irradiation conditions with a good weld joint will also be indicated by a minimum of the second spectral line and a simultaneous maximum of the third spectral line.

In the practical execution, the first spectral line (approx. 2 Mhz) is set to 1 and the height of the second spectral line is observed. If this height remains below threshold 26, the weld joint is in order, as pointed out above. Thus in practice the minimum amplitude (energy density) of the first spectral line is measured not in absolute but in relative terms. The weld joint is in order, if the first spectral line has a sufficient empirically determined size relative to the second spectral line. As in the case with threshold 20, threshold 22 is also measured and determined by comparison with sample weld points.

A comparison of the A-images (FIGS. 1 and 3) with the frequency representations (FIGS. 2 and 4) shows, that the frequency representations are easier to comprehend and thus easier to evaluate by a computer. The method according to the invention allows point welds to be inspected largely automatically.

The method according to the invention is also suitable for the inspection of weld joints with more than two sheets, for example with three sheets. The fact that the frequency representation is distinctly simpler and displays less detailed features than the A-images, which present a multitude of separate signals for more than two sheets, is a particularly positive advantage in this case.

We claim:

1. An ultrasonic method for the inspection of point welds between metal sheets, in which a high frequency test probe with a transducer diameter equal to the nominal diameter of the point weld to be inspected is coupled, with a lead section, to the sheets in the vicinity of the point weld and, using the pulse/echo method, the sheets are irradiated with ultrasonic signals and the echo pulse trains received are evaluated, characterized in that the frequency spectrum of the echo pulse trains is calculated and that for each measurement a spectral line corresponding to the overall-thickness travel time is examined on the one hand for sufficient minimum amplitude (energy density) and on the other hand for sufficient minimum width (attenuation).

2. A method according to claim 1, further characterized in that before the calculation of the frequency spectra the echo pulse trains are not rectified.

3. A method according to claim 1, wherein positioning of said test probe for achieving adequate irradiation conditions is achieved by setting a threshold value (22) in the time-domain representation (A-image) for the first echo pulse corresponding to the total travel time, and measuring the amplitude of said first echo pulse to determine if said threshold value has been surpassed.

4. A method according to claim 1, further characterized in that for the optimization of the irradiation conditions of the test probe spectral lines are observed in the frequency-domain representation, which are exclusively determined by the overall sheet thickness, making sure that the amplitude ratio of a higher order spectral line to a lower order spectral line is as high as possible; specifically in the case of two equally thick sheets, that the amplitude ratio of the third spectral line to the first spectral line is as high as possible.

5. A method according to any of the claim 1, further characterized in that under predetermined irradiation conditions the frequency spectrum is only then calculated by a Fourier transform, when the amplitude of the first back-wall echo in the time-domain representation lies above a threshold value (22) and/or the echo pulse signals from the overall thickness show a monotonous decay, i.e. the amplitude of the n+1-th echo pulse is smaller than the n-th echo pulse in the time image.

6. A method according to claim 1, further characterized in that in the frequency-domain representation a threshold (26) is provided for a spectral line from a single-sheet travel time, which must not be surpassed for a good weld point.

7. A method according to claim 1, further characterized in that the amplitude ratio between the spectral line from the overall-thickness travel time, and at least one spectral line from a single sheet travel time, is measured.

8. A method according to claim 1, further characterized in that a threshold (24) is established for a spectral line from the overall-sheet-thickness travel time in the frequency domain, which indicates the existence of adequate irradiation conditions.

9. A method according to claim 1, further characterized in that the spectral line from the overall-thickness travel time is monitored for a certain maximal width.

10. A method according to claim 1, further characterized in that a data reduction is performed to facilitate the computation of a Fourier transform.

11. A method according to claim 1, further characterized in that filtering is performed at the beginning and at the end of a selected time interval to avoid artificial frequency lines.

12. A method according to claim 1, further characterized in that the first spectral line is examined.

13. A method according to claim 7, wherein the amplitude ratio of the spectral line corresponding to the single sheet travel time, and the spectral line corresponding to the overall-thickness travel time, is measured.

* * * * *